(12) United States Patent
Maestro et al.

(10) Patent No.: US 8,709,502 B2
(45) Date of Patent: Apr. 29, 2014

(54) **EXTRACT OF *VANILLA PLANIFOLIA***

(75) Inventors: Yannick Maestro, le Cannet (FR);
Christelle Lasserre, Jersey City, NJ (US); Daniel Bergia, Valbonne (FR)

(73) Assignee: Chanel Parfums Beaute, Neuilly sur Seine (FR)

( * ) Notice: Subject to any disclaimer, the term of this patent is extended or adjusted under 35 U.S.C. 154(b) by 1650 days.

(21) Appl. No.: 11/534,888

(22) Filed: Sep. 25, 2006

(65) Prior Publication Data

US 2007/0071710 A1    Mar. 29, 2007

Related U.S. Application Data

(60) Provisional application No. 60/748,199, filed on Dec. 8, 2005.

(30) Foreign Application Priority Data

Sep. 23, 2005  (FR) ..................................... 05 09765
Sep. 23, 2005  (FR) ..................................... 05 09767

(51) Int. Cl.
*A61K 36/00*   (2006.01)
*A61K 8/97*    (2006.01)

(52) U.S. Cl.
USPC ............................................ 424/725; 424/74

(58) Field of Classification Search
None
See application file for complete search history.

(56) References Cited

U.S. PATENT DOCUMENTS

| 6,010,701 | A | 1/2000 | Matsukura et al. |
| 2002/0187245 | A1* | 12/2002 | McFadden et al. ............ 426/651 |
| 2004/0170590 | A1* | 9/2004 | Fahnestock et al. ........ 424/70.14 |
| 2004/0194793 | A1* | 10/2004 | Lindell et al. ................. 131/270 |

FOREIGN PATENT DOCUMENTS

| FR | 2 073 240 | 10/1971 |
| FR | 2 837 384 | 9/2003 |
| FR | 2837384 A1 * | 9/2003 |
| JP | 2005089395 A * | 4/2005 |
| WO | WO 2004/084855 | 10/2004 |

OTHER PUBLICATIONS

Ramaroson-Raonizafinimanana et al (1), Journal of agricultural and food chemistry, Jul. 1997. vol. 45, No. 7. p. 2542-2545.*
Ramaroson-Raonizafinimanana et al (2), Long-chain aliphatic beta-diketones from epicuticular wax of Vanilla bean species. Synthesis of nervonoylacetone, Journal of agricultural and food chemistry, (Oct. 2000) vol. 48, No. 10, pp. 4739-4743.*
Ramaroson-Raonizafinimanana et al (3), Long-chain gamma-pyrones in epicuticular wax of two vanilla bean species: *V. fragrans* and *V. tahitensis*, Journal of agricultural and food chemistry, (Aug. 1999) vol. 47, No. 8, pp. 3202-3205.*
Ramaroson-Raonizafinimanana et al (4), Ramaroson-Raonizafinimanana, 4-Demethylsterols and triterpene alcohols from two Vanilla bean species: *Vanilla fragrans* and *V. tahitensis*, Journal of the American Oil Chemists' Society, Jan. 1998. vol. 75, No. 1. p. 51-55.*
Fu et al, Study on components of vanilla extract by different extracting technology, Shipin Kexue (Beijing, China) (2002), 23 (3), 109-112.*
Mestres, Composition of vanilla extracts, Annales des Falsifications et des Fraudes (1954), 47, 82-4.*
*Vanilla planifolia* from Wikipedia, accessed on Aug. 24, 2011, pp. 1-2.*
Scheinman, Prevalence of fragrance allergy, Dermatology 2002; 205: 98-102.*
XP-002387752—Database WPI—Section CH, Week 200262—Derwent Publications Ltd., London, GB; AN 2002-580654, 2002.
Lamprecht, et al., "Determination of the Authenticity of Vanilla Extracts by Stable Isotope Ratio Analysis and Component Analysis by HPLC", J. Agric. Food Chem., vol. 42, p. 1722-1727, 1994.
Arvind S. Ranadive, "Vanillin and Related Flavor Compounds in Vanilla Extracts Made from Beans of Various Global Origins", J. Agric. Food Chem., vol. 40, p. 1922-1924, 1992.

* cited by examiner

*Primary Examiner* — Qiuwen Mi
(74) *Attorney, Agent, or Firm* — Young & Thompson

(57) ABSTRACT

The invention relates to an extract of *Vanilla planifolia*, consisting in a liposoluble fraction, to a cosmetic or dermatological composition containing it, and to cosmetic and dermatological methods using same, especially in the treatment of skin ageing.

12 Claims, No Drawings

EXTRACT OF *VANILLA PLANIFOLIA*

BACKGROUND OF THE INVENTION (i) Field of Invention

The invention relates to a novel extract of *Vanilla planifolia*, consisting in a liposoluble fraction, to a cosmetic or dermatological composition containing it, and to cosmetic and dermatological methods using same, especially in the treatment of skin ageing.

The skin consists mainly of three layers, i.e., starting from the most superficial, the epidermis, the dermis and the hypodermis.

The epidermis contributes largely to providing protection for the skin and to maintaining the trophicity thereof.

Aging and photoaging of the skin and the alterations which are associated therewith can manifest themselves in various ways, among which mention may be made of:
  loss of firmness and of elasticity due to a tissue loss in the epidermis and/or the dermis;
  loss of radiance due to the reduction in the microcirculation and to a slowing down of cell renewal in the epidermis;
  the appearance of pigmentary marks associated with a dysfunction of melanin synthesis (or melanogenesis);
  dryness of the skin resulting from a decrease in the barrier function of the cornefied layer and to a slowing down of epidermal renewal.

As a result, there exists a need to provide a polyfunctional active agent capable of acting on a set of causes of skin alterations due to aging and/or to a modification of the physiological mechanisms related to aging or related mechanisms.

(ii) Description of Related Art

Application FR 2 837 384 describes the use of extract of vanilla, preferably *Vanilla tahitensis*, for the preparation of cosmetic or pharmaceutical compositions for protecting the skin against solar radiation or against the generation of free radicals, these activities being associated with the presence of polyphenols contained in this extract.

SUMMARY OF THE INVENTION

It has now been found that an extract of *Vanilla planifolia*, consisting in a liposoluble fraction, had via the stimulation or inhibition of physiological mechanisms, activities capable of acting on the symptoms due to aging, or to physiological mechanisms related to aging, or to conditions related to these mechanisms in the epidermis and/or the dermis.

Surprisingly, these activities are not associated with the presence of polyphenols in this extract.

DETAILED DESCRIPTION OF PREFERRED EMBODIMENTS

According to a first aspect, the invention therefore relates to an extract of *Vanilla planifolia*, consisting in a liposoluble fraction. Preferably, said fraction comprises:
  0.5% to 10% of unsaturated monocarbonyl compounds,
  20% to 80% of unsaturated dicarbonyl compounds, and
  1% to 40% of unsaturated pyranones,
  said contents being expressed as relative percentages relative to all the constituents separated by gas chromatography.

The term "liposoluble fraction" is intended to mean the fraction which, when an extraction is carried out using a solvent, after milling and/or maceration of the vanilla, possibly followed by separation by settling out, using an organic solvent that brings about phase separation, is soluble in an oily phase and not in an aqueous phase. It relates more specifically to a fraction which is insoluble in water in an amount of at least 1% by weight at 25° C. and which is soluble in the same conditions in at least one apolar solvent having a polarity index less than 3.5, which may inter alia be chosen among: hexane, cyclohexane, heptane, isooctane and dichloromethane. The apolar solvent has preferably a polarity index less than 1 and is thus preferably chosen among: hexane, cyclohexane, heptane and isooctane.

The expression "content expressed as relative percentages relative to all the constituents separated by gas chromatography" is intended to mean that the content of each of the constituents is determined relative to all the constituents separated by the chromatographic system. The only compounds present are those extracted by the solvent during the sample preparation and which can vaporize in the injector.

The sample is preferably prepared according to the standard NF T 60-233 of May 1977 "Preparation of methyl esters of fatty acids" (§5.2—Method applicable to acid fatty substances and fatty acids). The chromatographic conditions are described in the standard NF EN ISO 5508 of June 1995.

Briefly, the method consists in esterifying the fatty acids in an acidic methanolic medium, then in extracting them with heptane, and then in injecting the heptane solution in gas chromatography.

Preferably, the extract of *Vanilla planifolia* according to the invention consists of a liposoluble fraction comprising:
  1% to 5% of unsaturated monocarbonyl compounds,
  35% to 65% of unsaturated dicarbonyl compounds, and
  3% to 25% of unsaturated pyranones, said proportions being expressed as relative percentages relative to all the constituents separated by gas chromatography.

According to preferred aspects of the invention, said extract comprises
  unsaturated monocarbonyl compounds chosen from Pentacos-16-en-2-one, Heptacos-18-en-2-one and Nonacos-20-en-2-one, and/or
  unsaturated dicarbonyl compounds chosen from Pentacos-16-ene-2,4-dione, Heptacos-18-ene-2,4-dione, Nonacos-20-ene-2,4-dione and Hentriacont-22-ene-2,4-dione, and/or
  unsaturated pyranones chosen from 2-nona-decenyl-2,3-dihydro-6-methyl-4-pyranone, 2-heneicosenyl-2,3-dihydro-6-methyl-4-pyranone and 2-tricosenyl-2,3-dihydro-6-methyl-4-pyranone.

In particular, said liposoluble fraction also comprises 5% to 50%, preferably 10% to 40% of saturated or unsaturated fatty acids, said proportions being expressed as relative percentages relative to all the constituents separated by gas chromatography.

Said extract also comprises, according to a preferred aspect, sterol compounds chosen from cholesterol, campesterol, stigmasterol and β-sitosterol.

It can alternatively or in addition comprise derivatives (including hydroxylated or alcoxylated) of benzaldehyde and in particular 4-hydroxy-3-methoxy-benzaldehyde or vanillin, preferably in an amount of from 0.1 to 10% by weight.

The starting material used consists, for example, of pods of vanilla of the species *Vanilla planifolia*, that can be ground or reduced to pieces in the usual manner.

The ground material can be subjected to an extraction with one or more solvents, for example chosen from $C_1$-$C_4$ alcohols such as, for example, methanol, ethanol, isopropanol, etc., organic solvents such as, for example, propylene glycol, dipropylene glycol, etc., or else ethyl acetate, hexane, cyclohexane or any other organic solvent that is usual in the field, or else with a supercritical fluid, preferably with supercritical $CO_2$. Alcoholic solvents are preferred.

The extraction is generally carried out by immersing or gently stirring the ground material in one or more of the solvents mentioned above, at temperatures ranging, for example, from ambient temperature to 100° C., for a period of approximately 30 min to 12 h.

The solution is then filtered in order to remove the insoluble substances of the plant. The solvent is also eliminated, where appropriate, if it is a volatile solvent such as, for example, ethanol, methanol, hexane, cyclohexane or ethyl acetate.

This extraction step is usual in the plant extract field, and those skilled in the art are able to adjust the reaction parameters thereof, on the basis of their general knowledge.

At the end of this extraction step, an oleoresin of vanilla is obtained.

According to an advantageous aspect of the invention, a fractionation step is carried out in order to purify the oleoresin.

A solvent or a mixture of solvents chosen from the solvents mentioned above will preferably be used, or preferably a hydroalcoholic solvent. Fractionation with a supercritical fluid, preferably with supercritical $CO_2$, can also be used.

As above, if one or more volatile solvents is (are) used, it will be necessary to eliminate it (them) before proceeding to the following step.

The liposoluble fraction originating either from the extraction, having used an appropriate extraction solvent, or, after separation by settling out, from the fractionation step mentioned above, is recovered.

Said liposoluble fraction can be used as the extract of *Vanilla planifolia* according to the invention.

Said liposoluble fraction can then, according to an advantageous aspect, be subjected to a molecular distillation (short-path distillation) step.

Wiped-film and short-path molecular distillation devices are preferred. They comprise a distillation chamber equipped with a revolving wiper, which allows the continuous spreading, over the evaporation surface (hot surface), of product to be distilled. The product vapors are condensed by means of a cold finger placed at the center of the distillation chamber. The residues and distillate are recovered by gravitational flow. The aim of this technique is to separate the constituents of the complex mixtures by taking advantage of their various boiling points. Wiped-film, short-path molecular distillation has the advantage of reducing the distillation temperature since the distillation is carried out under a strong vacuum, and of also reducing the amount of time spent by the mixture to be separated in the distillation device. In fact, the rate of decomposition of the products increases enormously as a function of the temperature and of the exposure time, and in an "alambic" type distillation device for example, the mixtures can spend hours at high temperatures, which leads to denaturation.

Up until now, in the case of plant oils, such a process had been used only for isolating unsaponifiable fractions or purifying these same plant oils by eliminating the unsaponifiable fractions, or else, in the case of water-soluble or liposoluble fractions, for decoloring or deodorizing the extracts.

However, it has now been found that, surprisingly, the use of a molecular distillation (short-path distillation) step makes it possible to isolate an oily distillate from a liposoluble fraction as described previously.

According to a preferred aspect, the method for obtaining an extract of *Vanilla planifolia* which may be used as a polyfunctional active according to the invention also comprises a step of molecular distillation (short-path distillation) of the liposoluble fraction, consisting preferably in:

subjecting the liposoluble fraction resulting from the aforesaid extraction to a molecular distillation (short-path distillation) at a temperature of between approximately 100 and 250° C. and a pressure of between approximately 0.1 and 0.001 mbar, and recovering the distillate.

Preferred conditions for implementing the method are given hereinafter:

Advantageously, a heavy solvent chosen from mineral or plant oils and polyols, such as, preferably, polyethylene glycol is added to the liposoluble fraction, before the distillation, so as to facilitate the distillation or the flow along the column.

The mixture of the liposoluble fraction and of the heavy solvent is introduced at a constant flow rate, at a temperature of between 20 and 120° C., preferably between 50 and 100° C., on the hot wall of a cylindrical evaporator.

Through scraping by means of rotary brush with rings, it is spread into a thin film over the entire surface of the hot wall maintained at a temperature of between approximately 100 and 250° C., and preferably between 150 and 220° C.

On contact with said wall, and under the very low pressure present in the evaporator, of the order of 0.1 mbar to 0.001 mbar, the volatile product is then partially and gradually vaporized, whereas the less volatile product flows along the wall.

The vapors emitted are condensed on the cold wall concentric with the hot wall and placed at a very short distance therefrom, preferably at a temperature of between 40 and 120° C., in particular between 60 and 100° C.

The products separated in the course of the process flow by gravity along the hot and cold walls.

The distillate is recovered and is subjected, where appropriate, to an additional separation process (filtration or centrifugation, for example).

An oily distillate is thus obtained, which may be used as a polyfunctional active according to the invention.

Advantageously, the extract (liposoluble fraction or oily distillate) used according to the invention is light in color. In addition, said extract is substantially deprived of, and preferably lacks, solvent or any other chemical reactant having been involved in the course of its extraction.

In addition, said extract is in a form sufficiently concentrated for it to be possible to use it without this leading to the problems of formulation normally encountered with the concentrations necessary for obtaining an activity in cosmetic or dermatological compositions in the form of an emulsion, and without being dark in color, contrary to the plant extracts obtained by the usual methods, which are in concentrated form.

As a result, the extract according to the invention can be used directly for the preparation of a cosmetic or dermatological composition.

The invention also relates to the extract of *Vanilla planifolia* that can be obtained by means of the method described above, i.e. according to a process comprising the steps consisting in:

extracting a ground material from *Vanilla planifolia* by means of at least one solvent, and recover the liposoluble fraction, and optionally comprising also a step of molecular distillation (short-path distillation) of the liposoluble fraction so as to obtain an oily distillate.

According to a subsequent aspect, the invention also relates to a cosmetic method for the prevention and/or treatment of alterations of the skin due to aging or to physiological mechanisms related to aging, or to conditions related to these mechanisms, comprising applying onto skin a composition comprising an extract of *Vanilla planifolia* according to this invention.

In fact, advantageously, it has been found that the extract of *Vanilla planifolia* according to the invention has several activities of interest with respect to preventive or repairing physiological mechanisms associated with alterations of the skin, due in particular to aging.

The invention therefore relates more particularly to a cosmetic method for improving skin atrophy and/or whitening skin and/or improving skin microcirculation and/or regenerating the epidermis and/or the dermis, comprising applying onto skin a composition comprising an extract of *Vanilla planifolia* according to this invention.

It also pertains to a method for depigmenting skin, comprising applying thereto an extract of *Vanilla planifolia* according to this invention.

The extract of *Vanilla planifolia* according to the invention may be used more specifically as an agent for inhibiting melanin synthesis, such as an agent for inhibiting endothelin synthesis.

It has also been found that, advantageously, the extract of *Vanilla planifolia* according to the invention exhibits an activating activity with regard to the synthesis of several families of growth factors by keratinocytes.

In particular, this activity is exerted with respect to the following growth factors:

FGF-b (basic fibroblast growth factor), also called FGFβ, b-FGF or FGF-2, which plays an important role in the maintenance and repair of numerous tissues, due to its ability to induce cell proliferation, in particular that of fibroblasts, keratinocyte migration essential during healing or during aging (Ashcroft G S et al., J. Anat, 1997, 190 (Pt 3): 351-65) and also antigenesis (Bikfalvi et al., Endocrine review, 1997, Vol 18 no. 1) or in response to UV irradiation (Kramer M et al., J. Biol. Chem., 1993, 268(9): 6734-41).

FGF-b is secreted and stored in the extra-cellular matrix in order to ensure all tissue repair. Furthermore, it plays a role in melanocyte proliferation and differentiation (Tada A et al., Cell, Growth Differ., 1998, 9(7): 575-84).

PDGF, or platelet-derived growth factor, which exerts in particular a mitogenic activity on most of the cells derived from the mesenchyme (Lepisto J et al., 1995, Biochem. Biophys. Res. Commun. 209(2): 393-9) and stimulates the synthesis of collagen and of collagenase by these cells, thus playing a role in physiological processes such as healing and tissue repair (Tan E M et al., Biochem. J. 1995, 310 (Pt 2): 585-8); it has also been shown that the level of induction of PDGFs and the replicative capacity of cells is related to age: the PDGF content of senescent fibroblasts decreases (Karlsson C et al., J. Cell Physiol., 1994, 158(2): 256-62). In addition, it has been shown that the amount and the type of the various growth factors could explain the differences in the ability of tissues to repair themselves with age (Ashcroft G S et al., J. Anat, 190, 1997, (Pt 3): 351-65).

TGFβ, or transforming growth factor β, which is a cytokine involved in the regulation of cell growth, and which plays a role in the regulation of keratinocyte growth (Yin L et al., J. Invest. Dermatol., 2003, 120(4): 703-5; Rittie L et al., Ageing Res. Rev., 2002, 1(4): 705-20), and in the synthesis of the extracellular matrix (Reed M J et al., J. Cell Physiol, 1994, 158(1): 169-79; Schiller M et al., J. Dermatol. Sci, 2004, 35(2): 83-92).

VEGF, or vascular endothelial growth factor, which represents, in the skin, a major skin angiogenesis factor. The epidermis is an important source of VEGF, secreted in large amounts by proliferating keratinocytes. VEGF mRNA is expressed by normal keratinocytes, both in a tissue in situ and in cell culture. It has been shown that VEGF would maintain the homeostatis of endothelial cells and their ability to respond to an angiogenic stimulation, even in elderly individuals (Watanabe Y et al., 1997, Oncogene 14: 2025-2032).

Furthermore, a decrease in VEGF has been observed following an exposure to UV radiation (Mildner M et al., Photochem. Photobiol., 1999; 70(4): 674-9).

HB-EGF, or heparin-binding epidermal growth factor, which plays an important role in keratinocyte regulation and differentiation (Iwamoto et al., Cytokine and Growth Factors Reviews, 2000, 11: 335-344), and also in the senescence of young cells whose growth depends on this factor (JID Suppl. 24: S46-S50; Kanzaki Y et al., Exp. Cell. Res., 2002, 279(2): 321-329).

The extract of *Vanilla planifolia* according to the invention, is especially useful as an agent for activating the synthesis of at least one cell growth factor by keratinocytes, in particular as an agent for activating at least one growth factor chosen from FGF-b, PDGF, TGFβ, VEGF and HB-EGF.

It is also useful as an agent for inhibiting the activity of matrix metalloproteinases (called MMPs).

Matrix metalloproteinases are enzymes which degrade the extracellular matrix in the context of physiological remodeling of the skin, but age and exposure to UV irradiation have the effect of increasing the activity of these MMPs, in particular that of MMP1, of MMP3 and of MMP9. As a result, the extracellular matrix is degraded to a great extent, with the result being sagging of the tissues of the skin and the formation of wrinkles (Rittie L et al., Ageing Res. Rev., 2002, 1(4): 705-20; Chung J H et al., J. Invest. Dermatol. 2001, 117(5): 1218-24).

According to a subsequent aspect, the invention also relates to a cosmetic or dermatological composition comprising an extract of *Vanilla planifolia* as described above and a cosmetically or pharmaceutically acceptable vehicle.

Preferably, said extract is present in the cosmetic or dermatological composition in a proportion of 0.001% to 10% by total weight of the composition, in particular in a proportion of 0.01% to 10%, preferably of 0.1% to 10% by total weight of the composition.

Said cosmetic or dermatological composition can in particular be suitable for topical application.

Advantageously, said cosmetic or dermatological composition can be in the form of a powder, an emulsion, a microemulsion, a nanoemulsion, a suspension, a solution, a lotion, a cream, an aqueous or aqueous-alcoholic gel, a foam, a serum, an aerosol solution or dispersion, or a dispersion of lipid vesicles.

In the case of an emulsion, it may be a water-in-oil or oil-in-water emulsion.

The cosmetic or dermatological composition according to the invention also comprises a solvent chosen according to the various ingredients and to the administration form.

By way of examples, mention may be made of water (preferably demineralized water), an alcohol such as ethanol, or a diethylene glycol ether such as ethoxydiglycol or diethylene glycol monomethyl ether.

Said cosmetic composition can also comprise at least one additive that is usual in the field, such as, for example, at least one compound chosen from an emollient or humectant, a gelling agent and/or thickener, a surfactant, an oil, an active agent, a dye, a preserving agent, an antioxidant, an active agent, an organic or inorganic powder, a sunscreen and a fragrance.

In particular, said composition can contain:

- One or more emollient(s) or humectant(s), which can be chosen, for example, from glycerine, glycols, water-soluble silicones such as that sold under the name KF6011 (Shin Etsu) and water-soluble jojoba, such as that sold under the name Resplanta jojoba (Res pharma).

Said emollient or humectant may be present in the composition at a content of the order of 0% to 30%, preferably 2% to 10% by total weight of the composition.

- One or more aqueous phase gelling agent(s) and/or thickener(s), chosen, for example, from cellulose derivatives, gums of plant origin (guar, carob, alginates, carrageenans, pectin) or of microbial origin (xanthan), clays (laponite), the materials identified by the INCI names, ammonium acryloyldimethyl taurate/vp copolymer and ammonium acryloyldimethyl taurate/beheneth-25 methacrylate copolymer (such as, for example, those sold under the names Aristoflex AVC and HMB by Clariant).

Said gelling agent and/or thickener may be present in the composition at a content of the order of 0% to 10% by total weight of the composition.

- One or more surfactant(s), preferably non-ionic, present at a content of the order of 0% to 8%, preferably 0.5% to 3% by total weight of the composition.

- One or more fatty substance(s) that is (are) liquid at ambient temperature, commonly called oil(s), that may be volatile or non-volatile, hydrocarbon-based or silicone-based, linear, cyclic or branched, for example isododecane, cyclopentadimethylsiloxane, dimethicone, isononyl isononanoate, pentaerythrityl tetraisostearate, etc., preferably in a proportion of 0% to approximately 10%, preferably 0.5% to 5% by total weight of the composition.

- One or more active agent(s) of natural, biotechnological or synthetic origin having a biological activity, for example chosen from vitamins, trace elements, allantoin, plant proteins, plant extracts, etc.

- One or more water-soluble dye(s) such as, for example, ponceau disodium salt, alizarine green disodium salt, quinoline yellow, amaranth trisodium salt, tartrazine disodium salt, rhodamine monosodium salt, fuchsin disodium salt or xanthophyll, preferably in a proportion of 0% to approximately 2% by total weight of the composition.

Other additives normally used in cosmetics can also be present in the composition according to the invention, in particular preserving agents, antioxidants or fragrances well known in the technical field.

Those skilled in the art are capable of choosing, among all these possible additives, both the type and the amount of those which will be added to the composition, in such a way that the latter conserves all its properties.

The invention is illustrated in a nonlimiting manner by the examples below.

Example 1

Method for Preparing an Extract According to the Invention

1) Alcoholic Extraction 0.5 kg of *Vanilla planifolia* pods are ground using a blade mill (Retsch) and loaded into a 5 l glass reactor equipped with a reflux.

2.5 l of ethanol at 96.3% are added and the mixture is heated for one hour. It is left to macerate in the cold overnight.

In the morning, the mixture is filtered and the reactor is emptied.

The solvent loaded is conserved. The vanilla ground material is again loaded into the reactor with 2.5 l of ethanol at 96.3%. The mixture is heated for 4 h at reflux at approximately 80° C.

The mixture is filtered and the reactor is emptied. The two filtrates are combined.

The solvent is then evaporated off with a rotary evaporator under vacuum.

0.155 kg of oleoresin of *Vanilla planifolia* is thus recovered.

Yield: 31%.

2) Taking up in Aqueous-Alcoholic Solution

Aqueous ethanol is prepared by mixing, under cold conditions, 96.3% ethanol and water (70/30 w/w).

The vanilla oleoresin obtained in the previous step is melted at 60° C. in order to facilitate dilution thereof.

8 kg of oleoresin are then mixed with 2 kg of aqueous ethanol and are mixed with the homogenizer until complete homogeneity is obtained.

After separation of the mixture by settling out for 72 h, a liposoluble supernatant appears in the upper portion.

The lower phase is removed and the upper phase is then recovered and the solvent is then evaporated from said solution under vacuum with a rotary evaporator.

2.38 kg of liposoluble fraction of *Vanilla planifolia* are thus obtained.

The yield from this process is 29.8%.

3) Molecular Distillation (Short-Path Distillation)

150 g of the liposoluble fraction of *Vanilla planifolia* obtained in the previous step are mixed with 50 g of polyethylene glycol 600 (INCI name: PEG12):

Two passes through a distillation apparatus of KDL4 type (UIC GmH) are then carried out according to the following distillation parameters:

| Distillation parameters | 1st pass | 2nd pass |
| --- | --- | --- |
| Insertion flow rate (ml/h) | 400 | 400 |
| Evaporator temperature (° C.) | 185 | 190 |
| Condenser temperature (° C.) | 75 | 75 |
| Product introduction temperature (° C.) | 75 | 75 |
| Stirring (rpm) | 180 | 180 |
| Vacuum pressure (mbar) | $2.2 \cdot 10^{-2}$ to $9.0 \cdot 10^{-3}$ | $2.2 \cdot 10^{-2}$ to $9.0 \cdot 10^{-3}$ |

The yields from the distillation are as follows, expressed relative to the weight of starting material:

Distillate 1st pass=18.53%

Distillate 2nd pass=8.67%

4) Centrifugation

The 1st pass distillate is recovered and left to separate by settling out, and then the supernatant is removed and centrifuged at approximately 4000 rpm for 10 min, and the upper phase loaded with oil is recovered.

The pellet from the separation by settling out is also run through the centrifuge and the upper phase loaded with oil is recovered.

After combining the various oils, the final 1st pass distillate is obtained, i.e. 24.22 g of oil.

The 2nd pass distillate does not contain any gum, and it is not therefore subjected to this centrifugation step.

All the oily fractions, i.e. the 1st pass and 2nd pass distillates, are combined, i.e. 24.22 g+13 g=37.22 g.

The yield from the molecular distillation (short-path distillation) and the centrifugation is 24.81%.

Example 2

Analysis of the Composition of the Extract of *Vanilla planifolia* According to the Invention 1) 100 mg of extract of *Vanilla planifolia* obtained as described in Example 1 are solubilized in 2 ml of a methanolic solution of 1N hydrochloric acid. The solution is placed, after stirring, in a waterbath at 80° C. for 10 min.

The esterified sample is recovered by liquid/liquid extraction with 2 ml of heptane and injected into the chromatograph.

The chromatography is carried out under the following conditions:

Gas chromatograph (Agilent series 6890).
Injector with or without division at 250° C.
Injection of 0.5 µl of sample prepared with a division of ¹⁄₁₀₀th.
Separation on a 100% grafted polydimethyl-siloxane capillary column, length 30 m, internal diameter 0.25 mm, film thickness: 0.25 µm (Agilent series DB-1).
Gas vector: helium at 1 ml/min.
Initial column oven temperature 70° C.
Temperature gradient from 70° C. to 250° C. at 2° C./min and isothermal at 250° C. for 60 min.
Total duration: 150 min.
Detection: flame ionization detector (auxiliary gas nitrogen).

The percentages given in Table 1 below are expressed as relative percentages obtained relative to all the constituents separated by the chromatographic system. Only the compounds extracted with hexane during the sample preparation and only the compounds that are able to vaporize in the injector are present in these results.

The constituents were identified by mass spectrometry.

The results are given in Table 1 below.

TABLE 1

| $T_R$ | Constituents | Relative % GC |
|---|---|---|
| 5.3 | Nonane | 0.10 |
| 34.3 | Methyl myristate | 0.09 |
| 37.7 | Methyl pentadecanoate | 0.16 |
| 41.0 | Methyl palmitate | 2.35 |
| 44.1 | Methyl heptadecanoate | 0.20 |
| 45.9 | Methyl linoleate | 6.42 |
| 46.0 | Methyl linolenate | 1.12 |
| 46.2 | Methyl oleate | 0.99 |
| 46.7 | Heneicosane | 0.09 |
| 47.1 | Methyl stearate | 0.52 |

TABLE 1-continued

| $T_R$ | Constituents | Relative % GC |
|---|---|---|
| 49.5 | Docosane | 0.09 |
| 51.5 | Tricosene | 0.33 |
| 52.4 | Tricosane | 0.38 |
| 52.7 | Methyl eicosanoate | 0.11 |
| 55.0 | Tetracosane | 0.22 |
| 56.8 | Pentacosene | 0.29 |
| 57.1 | Methyl docosen-13-oate | 0.17 |
| 57.5 | Pentacosane | 0.45 |
| 57.9 | Methyl docosanoate | 0.15 |
| 59.6 | Methyl tricosenoate | 0.17 |
| 60.3 | Hexacosane | 0.10 |
| 60.8 | Methyl tricosanoate | 0.10 |
| 61.7 | Pentacos-16-en-2-one | 0.51 |
| 62.2 | Methyl tetracosen-15-oate | 2.46 |
| 62.6 | Heptacosane | 0.41 |
| 63.0 | Methyl tetracosanoate | 0.29 |
| 64.5 | Pentacos-16-ene-2,4-dione | 1.66 |
| 64.9 | Methyl pentacosenoate | 0.52 |
| 65.9 | Octacosane | 0.11 |
| 66.6 | Methyl pentacosanoate | 0.15 |
| 68.5 | Heptacos-18-en-2-one | 0.47 |
| 69.0 | 2-Nonadecen-10-yl-2,3-dihydro-6-methyl-4H-pyran-4-one | 0.64 |
| 69.3 | Methyl hexacosenoate | 0.74 |
| 70.3 | Nonacosane | 0.07 |
| 70.5 | Methyl hexacosanoate | 0.10 |
| 70.8 | Methyl heptacosenoate | 1.17 |
| 72.7 | Methyl heptacosanoate | 0.22 |
| 73.1 | Heptacos-18-ene-2,4-dione (nervonoylacetone) | 38.14 |
| 76.8 | Triacontane | 2.33 |
| 79.4 | Methyl octacosenoate | 0.28 |
| 79.9 | Nonacos-20-en-2-one | 0.96 |
| 80.4 | 2-Heneicosen-12-yl-2,3-dihydro-6-methyl-4H-pyran-4-one | 2.68 |
| 81.0 | Methyl octacosenoate | 0.60 |
| 82.4 | Hentriacontane | 0.21 |
| 86.7 | Nonacos-20-ene-2,4-dione | 9.59 |
| 92.5 | Methyl triacontenoate | 1.05 |
| 98.9 | 2-Tricosen-14-yl-2,3-dihydro-6-methyl-4H-pyran-4-one | 6.47 |
| 109.0 | Hentriacont-22-ene-2,4-dione | 3.04 |
| | Total % GC | 89.47 |

Example 3

Study of the Activity of Extracts of *Vanilla planifolia* According to the Invention with Respect to the Growth Factor HB-EGF Firstly, an extract of *Vanilla planifolia* obtained according to Example 1, at the end of step 2, hereinafter referred to as "liposoluble fraction" was tested, and, secondly, an extract of *Vanilla planifolia* obtained at the end of step 4, hereinafter referred to as "oily distillate" was tested.

1/ Preparation of Keratinocyte Cultures

This protocol is common to all the biological activity assays.

Keratinocytes derived from neonatal foreskins (Clonetics, San Diego, USA) were seeded into 6-well plates and cultured in culture medium for keratinocyte growth (KBM, Clonetics), namely a modified culture medium supplemented with recombinant human EGF, insulin, hydrocortisone, bovine pituitary extract, gentamycin and amphotericin b.

After culture for 24 h in an incubator at 37° C., the confluent cells were washed with PBS buffer (Gibco) and incubated with specific basic medium (KBM, Clonetics) containing the products to be tested, for 24 h, at concentrations of 500, 10, 1 or 0.1 µg/ml. After studying the cytotoxicity of the extract, the activity thereof was evaluated. Not all these concentrations were necessarily tested in all the assays.

2/ Measurement of the HB-EGF Messenger RNA (mRNA) Expression

Principle of the Assay:

Real-time polymerase chain reaction (RT-PCR) is used to quantify the expression of the HB-EGF messenger RNA in a treated sample compared with a nontreated sample. The results are normalized relative to the expression of housekeeping genes in these samples and corrected with regard to the differences in PCR efficiency.

The results are expressed as number of times the target gene (HB-EGF) expression is increased or decreased in the treated sample, and not as absolute number of copies.

The sequences of the cDNAs/mRNAs of the genes investigated were obtained from GenBank.

Target gent: HB-EGF

Housekeeping gene: PBDG

All the PCR primers were obtained using the PRIMER3 software from the Whitehead Institute for Biomedical Research.

Assay Protocol:

The mRNA was isolated using the Trizol reagent (Invitrogen) according to the manufacturer's recommendations. The reverse transcription was carried out using the gene Amp RNA PCR kit (Applied Biosystems) according to the manufacturer's recommendations.

The real-time PCR measurement was carried out using the iCYCLER IQ device (Biorad) with SYBR Green I detection. In all the assays, the cDNA was amplified using a standardized program. Each sample was loaded with supermix IQ SYBR Green I, water and the primer (stock); the final amount of cDNA per reaction corresponded to 25 ng of total RNA used for the reverse transcription.

The specificity of the PCR was tested by agarose gel electrophoresis and evaluated for each sample using a melting point analysis included in the PCR program.

The relative quantification of the target gene expression was carried out using the Pfaffl mathematical model (Pfaffl, M W, Nucleic Acids Res. 29(9), p. E45, 2001).

The results are reported in Table 2 below:

TABLE 2

| Product tested | Concentration (µg/ml) | Activity (stimulation) |
|---|---|---|
| Liposoluble fraction | 10 | Non detectable |
| | 100 | 3.1 |
| | 500 | 12.6 |
| Oily distillate | 10 | 2 |
| | 100 | 4.7 |
| | 500 | 16.4 |

The results show that the extracts of *Vanilla planifolia* according to the invention have stimulatory activity with respect to the synthesis of the HB-EGF growth factor.

Example 4

Study of the Activity of Extracts of *Vanilla planifolia* According to the Invention with Respect to the TGF-β1 Growth Factor The quantitative evaluation of the concentrations of activated TGF-β1 growth factor in the cell cultures was carried out by means of the ELISA method using the Quantikine® immunoassay kit (No. DB100, R&D Systems).

The keratinocyte culture conditions and the samples tested are as described in Example 3.

The results are reported in Table 3 below:

TABLE 3

| Product tested | Concentration (µg/ml) | Activity (stimulation) |
|---|---|---|
| Liposoluble fraction | 1 | 100% |
| | 10 | 179% |
| Oily distillate | 1 | 132.6% |
| | 10 | 121% |

The results show that the extracts of *Vanilla planifolia* according to the invention have stimulatory activity with respect to the synthesis of the TGF-β1 growth factor.

Example 5

Study of the Activity of Extracts of *Vanilla planifolia* According to the Invention with Respect to the VEGF Growth Factor The quantitative evaluation of the concentrations of VEGF growth factor in the cell cultures was carried out by means of the ELISA method using the Quantikine® immunoassay kit (No. DVE00, R&D Systems).

The keratinocyte culture conditions and the samples tested are as described in Example 3.

The results are reported in Table 4 below:

TABLE 4

| Product tested | Concentration (µg/ml) | Activity (stimulation) |
|---|---|---|
| Liposoluble fraction | 0.1 | 168.5% |
| | 1 | 179.4% |
| | 10 | 155.8% |
| | 100 | 200% |
| | 500 | 200.3% |
| Oily distillate | 0.1 | 145.9% |
| | 1 | 158.1% |
| | 10 | 170.6% |
| | 100 | 187.8% |
| | 500 | 198.1% |

The results show that the extracts of *Vanilla planifolia* according to the invention have stimulatory activity with respect to the synthesis of the VEGF growth factor.

Example 6

Study of the Activity of Extracts of *Vanilla planifolia* According to the Invention with Respect to the PDGF-AA Growth Factor The quantitative evaluation of the concentrations of human PDGF-AA growth factor in the cell cultures was carried out by means of the ELISA method using the Quantikine® immunoassay kit (No. DAA00, R&D Systems).

The keratinocyte culture conditions and the samples tested are as described in Example 3.

The results are reported in Table 5 below:

TABLE 5

| Product tested | Concentration (μg/ml) | Activity (stimulation) |
|---|---|---|
| Liposoluble fraction | 0.1 | 133.8% |
| | 1 | 131.8% |
| | 10 | 137.0% |
| Oily distillate | 0.1 | 137.1% |
| | 1 | 131.8% |
| | 10 | 145.8% |

The results show that the extracts of *Vanilla planifolia* according to the invention have stimulatory activity with respect to the synthesis of the PDGF-AA growth factor.

Example 7

Study of the Activity of Extracts of *Vanilla planifolia* According to the Invention with Respect to the FGF-b Growth Factor The quantitative evaluation of the concentrations of human FGF-b growth factor in the cell cultures was carried out by means of the ELISA method using the Quantikine® immunoassay kit (No. DFB50, R&D Systems).

The keratinocyte culture conditions and the samples tested are as described in Example 3.

The results are reported in Table 6 below:

TABLE 6

| Product tested | Concentration (μg/ml) | Activity (stimulation) |
|---|---|---|
| Liposoluble fraction | 10 | 100% |
| | 100 | 321.1% |
| | 500 | 433.3% |
| Oily distillate | 10 | 484.8% |
| | 100 | 175.8% |
| | 500 | 145.8% |

The results show that the extracts of *Vanilla planifolia* according to the invention have stimulatory activity with respect to the synthesis of the FGF-b growth factor.

Example 8

Study of the Activity of Extracts of *Vanilla planifolia* According to the Invention with Respect to Endothelin-1

The quantitative evaluation of the concentrations of human endothelin-1 in the cell cultures was carried out by means of the ELISA method using the Quantikine® immunoassay kit (No. BEES, R&D Systems).

The keratinocyte culture conditions and the samples tested are as described in Example 3.

The results are reported in Table 7 below:

TABLE 7

| Product tested | Concentration (μg/ml) | Activity (stimulation) |
|---|---|---|
| Liposoluble fraction | 10 | 0% |
| | 100 | 75.7% |
| | 500 | 72.2% |

TABLE 7-continued

| Product tested | Concentration (μg/ml) | Activity (stimulation) |
|---|---|---|
| Oily distillate | 10 | 27.8% |
| | 100 | 82.9% |
| | 500 | 94.9% |

The results show that the extracts of *Vanilla planifolia* according to the invention have inhibitory activity with respect to the synthesis of endothelin-1.

Example 9

Study of the Activity of Extracts of *Vanilla planifolia* According to the Invention with Respect to Matrix Metalloproteases (MMPs)

Principle of the Assay

The products to be tested are incubated with the activated MMPs. The enzymatic activity is controlled by the addition of a fluorescent enzymatic substrate specific for each MMP.

Assay Protocol pro-MMP1, pro-MMP2 or pro-MMP9 are incubated in plates with a solution of APMA (p-aminophenylmercuric acetate) at ambient temperature, with gentle shaking, for 1 h.

Various concentrations of the various potential inhibitors are added. The mixture is then incubated at ambient temperature with gentle shaking. The enzymatic reaction is initiated by adding the fluorescent substrate solubilized in DMSO.

The enzymatic reaction is followed for 1 h by means of a spectrofluorimeter and the fluorescence is measured at an excitation wavelength of 360 nm and an emission wavelength of 460 nm for MMP1; and at an excitation wavelength of 320 nm and an emission wavelength of 405 nm for MMP2 and MMP9.

The results are expressed in units of fluorescence emitted (RFU) which represents the amount of substrate hydrolyzed per min.

The Microwin 2000 spectrofluorimeter calculates the variation in absorbance Δ, which represents the initial rate (Vi) of the enzymatic reaction. In each assay, the mean of 3 values of Vi obtained for each concentration of potential inhibitor is calculated. The results of 10 experiments were expressed as mean±SD, and then presented as percentage residual activity.

The results are reported in Tables 8-10 below:

TABLE 8

| Product tested | Concentration (μg/ml) | Activity (inhibition) ou MMP1 |
|---|---|---|
| Liposoluble fraction | 100 | 53% |
| | 500 | 94% |
| | 1000 | 99% |
| Oily distillate | 100 | 27% |
| | 500 | 72% |
| | 1000 | 91% |

The results show that the extracts of *Vanilla planifolia* according to the invention have MMP1-inhibiting activity.

TABLE 9

| Product tested | Concentration (μg/ml) | Activity (inhibition) ou MMP2 |
|---|---|---|
| Liposoluble fraction | 10 | 0% |
| | 100 | 37% |
| | 500 | 88% |
| | 1000 | 94% |
| Oily distillate | 10 | 21% |
| | 100 | 33% |
| | 500 | 62% |
| | 1000 | 78% |

The results show that the extracts of *Vanilla planifolia* according to the invention have MMP2-inhibiting activity.

TABLE 10

| Product tested | Concentration (μg/ml) | Activity (stimulation) ou MMP9 |
|---|---|---|
| Liposoluble fraction | 100 | 536% |
| | 500 | 84% |
| | 1000 | 96% |
| Oily distillate | 100 | 23% |
| | 500 | 60% |
| | 1000 | 75% |

The results show that the extracts of *Vanilla planifolia* according to the invention have MMP9-inhibiting activity.

Example 10

Oil-in-Water Emulsions (O/W)

The following compositions can be prepared in a usual manner for the man skilled in the art. The amounts indicated below are expressed as weight percentages.

| Emulsion A | |
|---|---|
| Cetearyl alcohol & cetearyl glucoside | 4.00% |
| Beheneth-25 | 2.00% |
| Liposoluble fraction of Vanilla planifolia* | 1.00% |
| Licorice extract | 0.10% |
| Emollients | 35.00% |
| Tocopheryl acetate | 0.50% |
| Dimethicone | 2.00% |
| EDTA | 0.05% |
| Glycerin | 5.00% |
| Gelling agents | 2.00% |
| pH adjustor | qs |
| Preservatives | qs |
| Water | qsp 100.00 % |

| Emulsion B | |
|---|---|
| Beheneth-25 | 2.00% |
| Oily distillate of Vanilla planifolia* | 0.10% |
| Hydrocotyl extract | 0.20% |
| Tightening agent | 5.00% |
| Emollients | 15.00% |
| UV filters | 0.50% |
| Tocopheryl acetate | 0.50% |
| Cyclomethicone | 5.00% |
| EDTA | 0.05% |
| Glycerin | 5.00% |
| Gelling agents | 5.00% |
| pH adjustor | qs |
| Preservatives | qs |
| Water | qsp 100.00% |

*prepared as described in Example 1

The invention claimed is:

1. A cosmetic composition, comprising an extract of *vanilla planifolia* obtained by a method comprising:
    extracting ground material of *vanilla planifolia* with at least one solvent selected from water and C1-C4 alcohol, to obtain an extracted solution,
    filtering the extracted solution,
    eliminating the solvent from the extracted solution to obtain an oleoresin of vanilla,
    fractionating the oleoresin of vanilla with at least one solvent selected from water and C1-C4 alcohol, in order to purify the oleoresin,
    settling out and eliminating the solvent and recovering a liposoluble fraction of the oleoresin,
    subjecting the liposoluble fraction to molecular distillation at a temperature of between approximately 100° C. and 250° C. and a pressure of between approximately 0.1 and 0.001 mbar, and
    recovering the distillate,
    wherein the obtained extract of *vanilla planifolia* is devoid of vanillin.

2. The cosmetic composition according to claim 1, wherein the liposoluble fraction comprises:
    1-5% of unsaturated monocarbonyl compounds;
    35-65% of unsaturated dicarbonyl compounds; and
    3-25% of unsaturated pyranones, said percentages being relative to all constituents separated by gas chromatography.

3. The cosmetic composition according to claim 2, wherein the unsaturated monocarbonyl compounds are selected from the group consisting of: pentacos-16-en-2-one; heptacos-18-en-2-one and nonacos-20-en-2-one.

4. The cosmetic composition according to claim 2, wherein the unsaturated dicarbonyl compounds are selected from the group consisting of: pentacos-16-ene-2,4-dione; heptacos-18-ene-2,4-dione; nonacos-20-ene-2,4-dione and hentriacont-22-ene-2,4-dione.

5. The cosmetic composition according to claim 2, wherein the unsaturated pyranones are selected from the group consisting of: 2-nonadecenyl-2,3-dihydro-6-methyl-4-pyranone; 2-heneicosenyl-2,3-dihydro-6-methyl-4-pyranone and 2-tricosenyl-2,3-dihydro-6-methyl-4-pyranone.

6. The cosmetic composition according to claim 1, wherein the liposoluble fraction comprises 10-40% of saturated or unsaturated fatty acids, said percentage being relative to all constituents separated by gas chromatography.

7. The cosmetic composition according to claim 1, wherein the liposoluble fraction comprises sterol compounds selected from the group consisting of: cholesterol, campesterol, stigmasterol and β-sitosterol.

8. The cosmetic composition according to claim 1, wherein the liposoluble fraction is subjected to molecular distillation at a temperature of between 150° C. and 220° C.

9. The cosmetic composition according to claim 1, comprising 0.1% to 10% by weight of the extract.

10. The cosmetic composition according to claim 1, formulated for topical application.

11. The cosmetic composition according to claim 1, wherein the ground material of *vanilla planifolia* is extracted with a solvent comprising ethanol.

12. The cosmetic composition according to claim 1, wherein the liposoluble fraction is subjected to molecular distillation a pressure of between 0.022 and 0.009 mbar.

* * * * *